US00PP32560P2

(12) United States Plant Patent
Hartman

(10) Patent No.: US PP32,560 P2
(45) Date of Patent: Dec. 1, 2020

(54) ***CALADIUM* PLANT NAMED 'OF13-635'**

(50) Latin Name: ***Caladium* X *hortulanum***
Varietal Denomination: OF13-635

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 16/873,507

(22) Filed: Apr. 23, 2020

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — C. A. Whealy

(57) ABSTRACT

A new and distinct cultivar of *Caladium* plant named 'OF13-635', characterized by its upright plant habit; intermediate height; dense and bushy appearance; vigorous growth habit and rapid growth rate; fancy-type leaves that are purplish red and purplish pink in color on a dark green-colored background, venation that is dark green blushed with dark greyish red in color and random white-colored spots; and petioles that are tannish pink in color with dark brown-colored stripes and tessellations or dark brown to almost black in color with tannish pink-colored stripes.

5 Drawing Sheets

Figure 1:
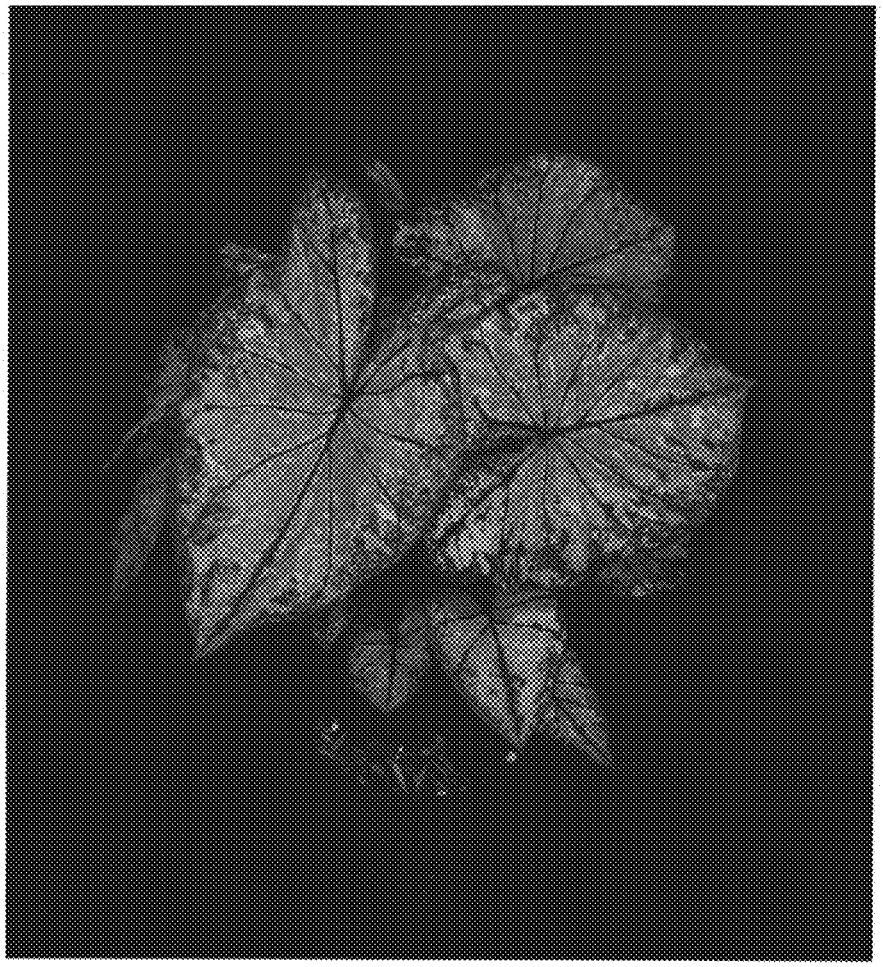

Botanical designation: *Caladium* X *hortulanum*.
Cultivar denomination: 'OF13-635'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'OF13-635'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2012 in Avon Park, Fla. of *Caladium* X *hortulanum* 'White Christmas', not patented, as the female, or seed, parent with *Caladium* X *hortulanum* 'Burning Heart', disclosed in U.S. Plant Pat. No. 27,071, as the male, or pollen, parent. The new *Caladium* plant was discovered and selected by the Inventor as a single plant within the progeny of the stated cross-pollination in a controlled outdoor nursery environment in Avon Park, Fla. in September, 2013.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2014 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'OF13-635'. These characteristics in combination distinguish 'OF13-635' as a new and distinct *Caladium* plant:

1. Intermediate in height and upright plant habit; dense and bushy appearance.
2. Vigorous growth habit and rapid growth rate.
3. Fancy-type leaves that are purplish red and purplish pink in color on a dark green-colored background, venation that is dark green blushed with dark greyish red in color and random white-colored spots.
4. Petioles that are tannish pink in color with dark brown-colored stripes and tessellations or dark brown to almost black in color with tannish pink-colored stripes.

Plants of the new *Caladium* differ primarily from plants of the female parent, 'White Christmas', in the following characteristics:

1. Plants of the new *Caladium* and 'White Christmas' differ in leaf color as leaves of the new *Caladium* are purplish red and purplish pink in color on a dark green-colored background, venation that is dark green blushed with dark greyish red in color and random white-colored spots whereas leaves of 'White Christmas' have distinct dark green-colored venation with white-colored interveinal areas that are often tinged with pink and dark green-colored borders.
2. Plants of the new *Caladium* and 'White Christmas' differ in leaf petiole color as leaf petioles of the new *Caladium* are tannish pink in color with dark brown-colored stripes and tessellations or dark brown to almost black in color with tannish pink-colored stripes whereas leaf petioles of 'White Christmas' are green in color with black-colored streaks.

Plants of the new *Caladium* differ primarily from plants of the male parent, 'Burning Heart', in the following characteristics:

1. Plants of the new *Caladium* and 'Burning Heart' differ in leaf color as leaves of the new *Caladium* are purplish red and purplish pink in color on a dark green-colored background, venation that is dark green blushed with dark greyish red in color and random white-colored spots whereas leaves of 'Burning Heart' are bronze in color with contrasting salmon orange-colored spots.
2. Plants of the new *Caladium* and 'Burning Heart' differ in leaf petiole color as leaf petioles of the new *Caladium* are tannish pink in color with dark brown-colored stripes and tessellations or dark brown to almost black in color with tannish pink-colored stripes whereas leaf petioles of 'Burning Heart' are green in color with faint brown-colored markings.

Plants of the new *Caladium* can be compared to plants of *Caladium* X *hortulanum* 'Florida Moonlight', disclosed in U.S. Plant Pat. No. 14,565. In side-by-side comparisons, plants of the new *Caladium* differ primarily from plants of 'Florida Moonlight' in the following characteristics:

1. Plants of the new *Caladium* are more upright than and not as mounding as plants of 'Florida Moonlight'.
2. Plants of the new *Caladium* and 'Florida Moonlight' differ in leaf color as leaves of the new *Caladium* are purplish red and purplish pink in color on a dark green-colored background, venation that is dark green blushed with dark greyish red in color and random white-colored spots whereas leaves of 'Florida Moonlight' have greenish white-colored leaves and venation.
3. Plants of the new *Caladium* and 'Florida Moonlight' differ in leaf petiole color as leaf petioles of the new *Caladium* are tannish pink in color with dark brown-colored stripes and tessellations or dark brown to almost black in color with tannish pink-colored stripes whereas leaf petioles of 'Florida Moonlight' are tan in color with green-colored tessellations.

Plants of the new *Caladium* can also be compared to plants of *Caladium* X *hortulanum* 'Candidum Senior', not patented. In side-by-side comparisons, plants of the new *Caladium* differ primarily from plants of 'Candidum Senior' in the following characteristics:

1. Plants of the new *Caladium* and 'Candidum Senior' differ in leaf color as leaves of the new *Caladium* are purplish red and purplish pink in color on a dark green-colored background, venation that is dark green blushed with dark greyish red in color and random white-colored spots whereas leaves of 'Candidum Senior' are greenish white in color with medium green-colored venation and thin green-colored margins.
2. Plants of the new *Caladium* and 'Candidum Senior' differ in leaf petiole color as leaf petioles of the new *Caladium* are tannish pink in color with dark brown-colored stripes and tessellations or dark brown to almost black in color with tannish pink-colored stripes whereas leaf petioles of 'Candidum Senior' are tan in color with greenish brown-colored tessellations.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1 of 7) is a side perspective view of a typical plant of 'OF13-635' in a container and grown in a shade house (tuber de-eyed).

Figure 2:
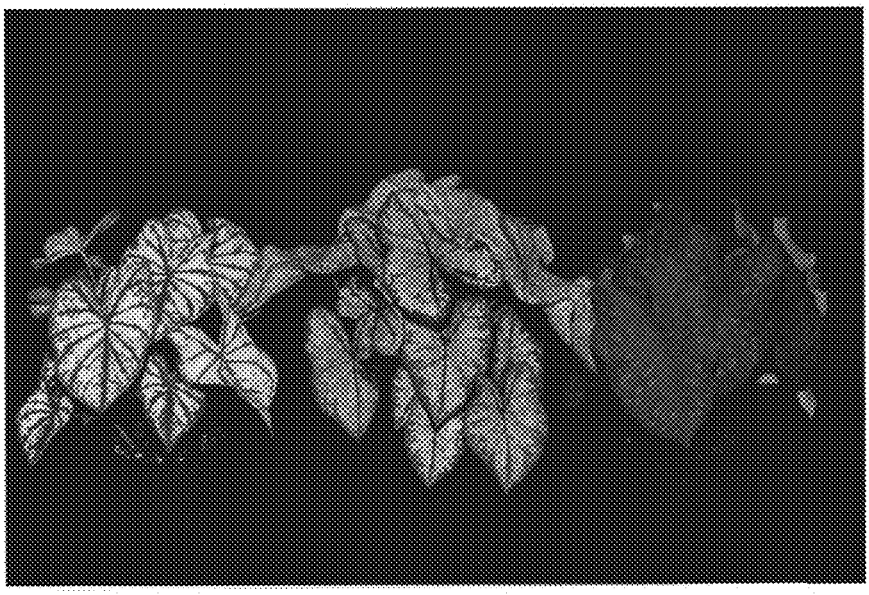

The photograph at the top of the second sheet (FIG. 2 of 7) is a comparison view of typical potted plants of the female parent, 'White Christmas' (left), 'OF13-635' (center) and the male parent, 'Burning Heart' (right).

Figure 3:
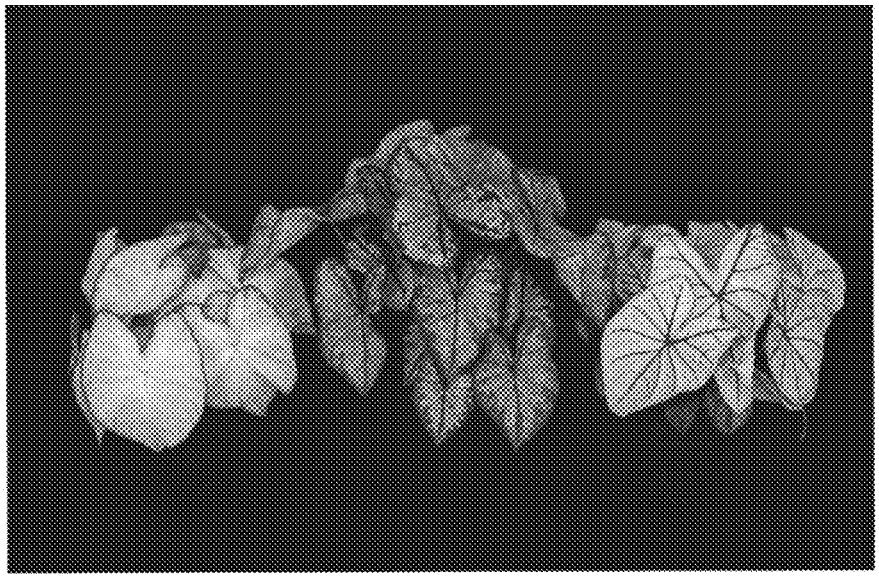

The photograph at the bottom of the second sheet (FIG. 3 of 7) is a comparison view of typical potted plants of 'Florida Moonlight' (left), 'OF13-635' (center) and 'Candidum Senior' (right).

Figure 4:
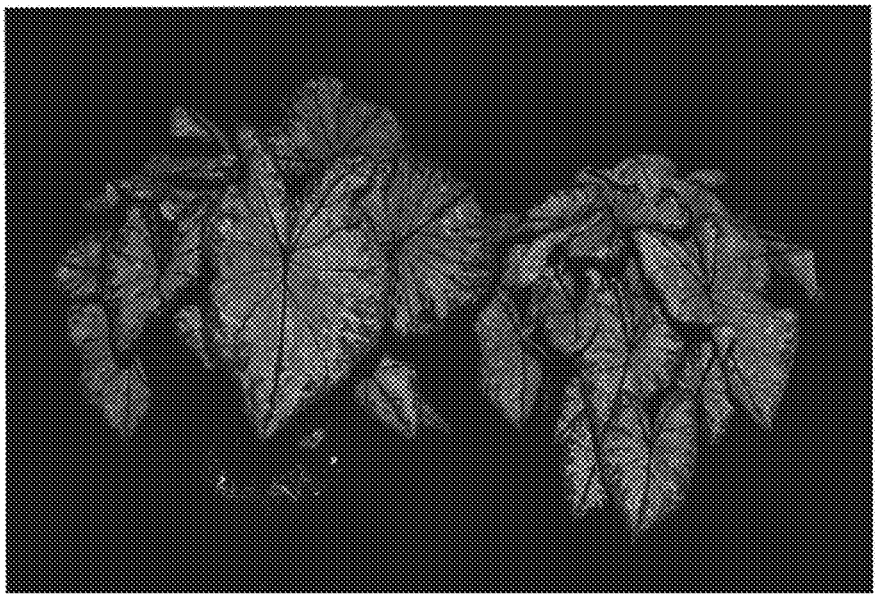

The photograph at the top of the third sheet (FIG. 4 of 7) is a comparison view of typical plants of 'OF13-635' grown in containers, the plant on the left has not had its tuber de-eyed and the plant on the right has had its tuber de-eyed prior to planting.

Figure 5:
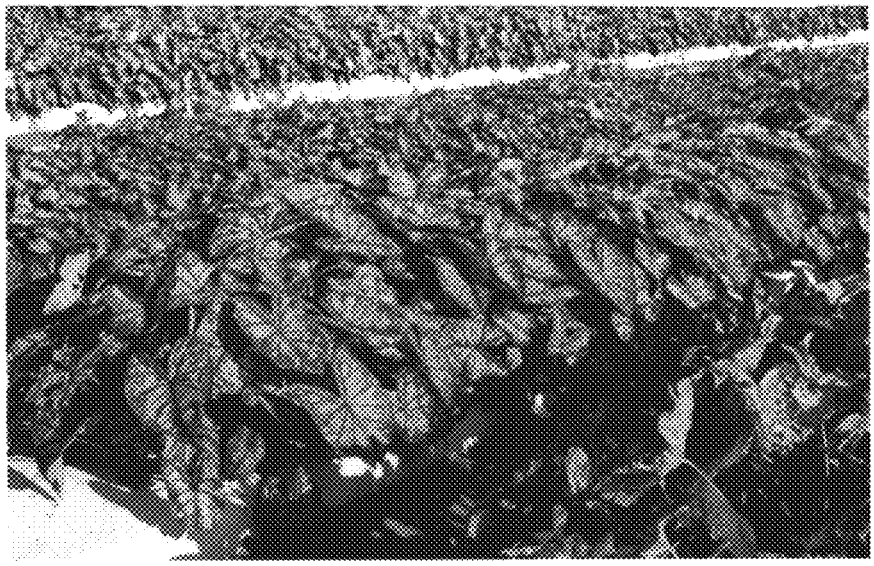

The photograph at the bottom of the third sheet (FIG. 5 of 7) is a side perspective view of typical plants of 'OF13-635' grown in an open production field.

Figure 6:
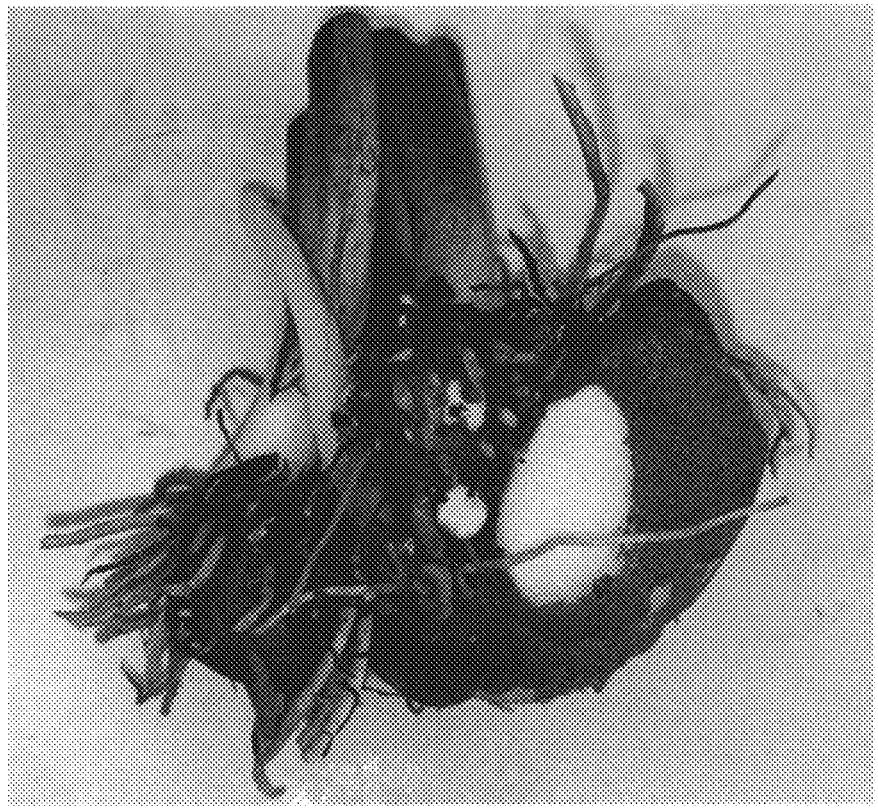

The photograph on the fourth sheet (FIG. 6 of 7) is a close-up view of typical freshly-harvested tubers with roots and leaf petioles of 'OF13-635'.

Figure 7:
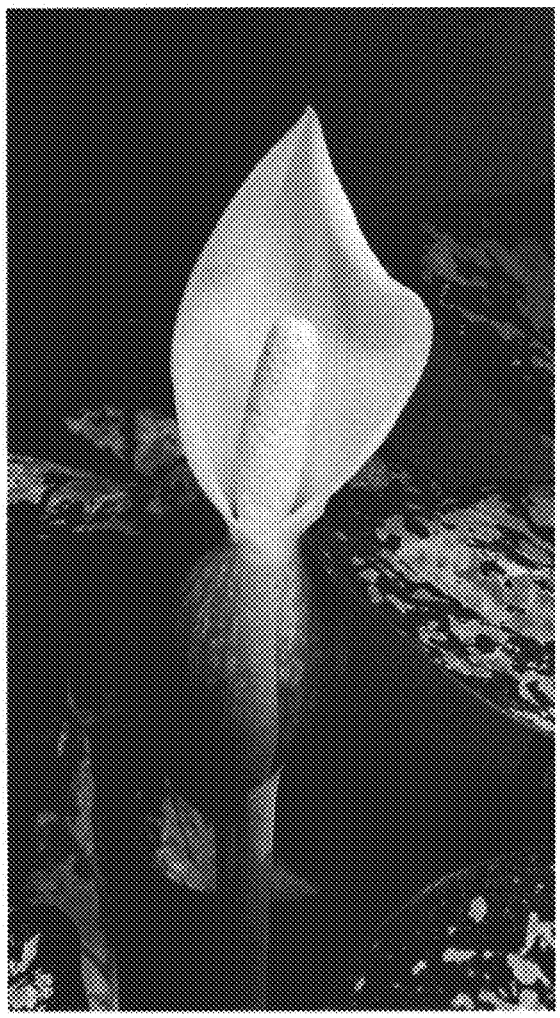

The photograph on the fifth sheet (FIG. 7 of 7) is a close-up view of a typical inflorescence of 'OF13-635'.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shade house were four weeks old and plants grown in the outdoor nursery were six months old when the photographs and the detailed description were taken. In the following description, color references are made to The Royal Horticultural Society Colour Chart, 2015 Edition, except where general terms of ordinary dictionary significance are used.

Botanical classification: *Caladium* X *hortulanum* 'OF13-635'.

Parentage:

*Female, or seed, parent.*—*Caladium* X *hortulanum* 'White Christmas', not patented.

*Male, or pollen, parent.*—*Caladium* X *hortulanum* 'Burning Heart', disclosed in U.S. Plant Pat. No. 27,071.

Propagation:

*Type*.—By "chipping" the tubers.

*Time to initiate roots, summer*.—About seven to ten days at temperatures about 32° C.

*Time to initiate roots, winter*.—About two to three weeks at temperatures about 24° C.

*Tuber description* (*outdoor nursery-grown plants*).—Appearance: Multi-segmented; individual segments elliptic in shape. Height: About 4.5 cm. Diameter: About 6 cm to 8.2 cm. Segment height: About 2.2 cm. Segment diameter: About 2.3 cm. Axillary bud shape: Roughly triangular. Axillary bud size: About 3 mm by 3.5 mm. Texture: Thick, starchy; somewhat brittle. Color: Periderm, freshly-harvested: Close to 199A. Periderm, dried: Close to 200A to 200B. Epidermis: Initially, close to 159C to 159D becoming closer to 159C with development. Cortical tissue: Close to 8D. Axillary buds: Close to 38C. Root description: Moderately thick, fleshy contractile roots with few lateral branches; color, close to N155D. Rooting habit: Medium density.

Plant description:

*Plant type*.—Herbaceous perennial; suitable as a potted plant in containers 15-cm to 25-cm and suitable as a landscape plant in shaded areas.

*Plant and growth habit*.—Intermediate in height and upright plant habit; dense and bushy appearance; vigorous growth habit and rapid growth rate; potted plants finish in saleable form in about four weeks after planting tubers; leaf petioles and leaves arise from one or more growing points on tubers; leaf petioles initially upright and somewhat outwardly leaning with development.

*Plant height, from soil level to top of foliar plane, shade house-grown potted plants*.—About 38 cm to 41 cm.

*Plant height, from soil level to top of inflorescences, shade house-grown potted plants*.—About 40.5 cm.

*Plant diameter or spread, shade house-grown potted plants*.—About 40 cm to 45 cm.

*Number of shoots per plant, shade house-grown potted plants, tubers not de-eyed*.—About four to five develop per #1 tuber.

*Number of shoots per plant, shade house-grown potted plants, tubers de-eyed*.—About four to five develop per #1 tuber.

*Cataphylls, shade house-grown potted plants*.—Length: About 6.3 cm to 10.5 cm. Width: About 1.4 cm to 1.8 cm. Shape: Lanceolate. Apex: Acute or emarginate. Base: Sheathing the stem. Color, outer surface: Initially close to N170D and 49D with variable stippling, streaks and marbling, close to 202A and 200A and towards the apex, close to 185B; with development, color becoming closer to 200C faintly tinged with close to 187C. Color, inner surface: Close to N155B and 196D; colors and patterns on outer surface visible on inner surface.

Leaf description:

*Arrangement and type*.—Alternate; simple; fancy-type.

*Length, shade house-grown potted plants*.—About 18 cm to 27.9 cm.

*Width, shade house-grown potted plants*.—About 13 cm to 17.6 cm; when flattened, about 13.5 cm to 18 cm.

*Shape*.—Ovate, cordate.

*Apex*.—Acute to cuspidate.

*Base*.—Sagittate-peltate, cordate.

*Margin*.—Entire; mostly flat with broad undulations.

*Texture and luster, upper surface*.—Glabrous, interveinal areas convex and concave; leathery; dull sheen.

*Texture and luster, lower surface*.—Glabrous, interveinal areas convex and concave; leathery; dull sheen and veins, glaucous.

*Venation pattern*.—Pinnate.

*Color, shade house-grown potted plants*.—Developing and fully developed leaves, upper surface: Background color: Close to 147A with a suffusion of speckles, close to 155C. Towards the margins: Close to 147A with a suffusion of speckles, close to 155C. Leaf edge: Narrow, close to 187B. Basal notch: Close to 187B. Leaf attachment point: Close to 147A flushed with close to N186C. Midvein and lateral venation: Close to 147A and close to 147A flushed with close to N186C and surrounded by close to 155C; smaller veins, close to N155B. Interveinal areas: Close to 54A, 54B and 54C. Random spots and blotches: Close to 155C, 54A and 54B. Developing and fully developed leaves, lower surface: Background color: Close to 191A with a suffusion of speckles, close to 155D and spots, close to 50D and 54B. Towards the margins: Close to 191A with a suffusion of speckles, close to 155D and spots, close to 50D and 54B. Leaf edge: Narrow, close to 187B. Basal notch: Close to 187B. Leaf attachment point: Close to 187C. Midvein: Close to 196A tinged with close to N186C surrounded by close to 191A. Lateral venation: Close to 191A tinged with close to N186C or 187B and surrounded by close to 191A; smaller veins, close to 55D and N155B. Interveinal areas: Close to 54A to 54B, 50D and 190A. Random spots and blotches: Close to 155D, 50D, 54A to 54B and 190A.

*Petioles*.—Aspect: Initially upright and straight and leaning outwardly with development; flexible. Length, shade house-grown potted plants: About 27 cm to 33 cm. Diameter, distally, shade house-grown potted plants: About 4.5 mm. Diameter, proximally, shade house-grown potted plants: About 6.5 mm to 8.5 mm. Texture and luster: Smooth, glabrous; glaucous. Color, shade house-grown potted plants: When developing and fully developed: Close to 182D, 49C and 49D with stippling and tessellations of close to 202A or close to 202A and 200A with stripes and streaks, close to 182D. Wing length, shade house-grown potted plants: About 4.3 cm to 6.9 cm. Wing diameter, shade house-grown potted plants: About 8 mm to 10 mm. Texture and luster, inner and outer surfaces: Smooth, glabrous; dull. Wing color, shade house-grown potted plants: Outer surface: Close to 155C and 49D with stippling, streaks and marbling of close to 200A and 202A; apex variably flushed with close to 185B. Inner surface: Close to N155B to N155C and 196D; colors and patterns on the outer surface are visible on the inner surface.

Inflorescence description: Inflorescences observed on seven week-old shade house-grown potted plants.

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with mint note.

*Natural flowering season and flower longevity*.—Plants of the new *Caladium* typically flower during the spring and summer in central Florida; flowers develop about seven weeks after growth commences; inflorescences last about three days before fading; inflorescences persistent.

*Spathe*.—Length, overall: About 10.5 cm. Length, distal open portion: About 6 cm. Length, proximal closed portion: About 4.5 cm. Width, distal open portion: About 4 cm. Depth, distal open portion: About 2.4 cm. Width, at constriction: About 1.5 cm. Width, proximal closed portion: About 2.8 cm. Shape, open portion: Ovate to elliptic. Apex: Acute. Base: Acute. Margin: Entire; smooth. Texture and luster, front surface: Smooth, glabrous; dull. Texture and luster, rear surface: Smooth, glabrous; dull, proximally, glaucous. Color, front surface: Distal open portion: Close to 155C; with development, color becoming closer to 199C to 199D. Proximal closed portion: Close to 194A and 147C; towards the base, darkly flushed with close to 187A; color does not change with development. Color, rear surface: Distal open portion: Close to 145D, mottled and marbled with close to 155C; color does not change with development. Proximal closed portion: Close to 147B, 147C and 147D with mottling and flecks of close to 148C and 148D, edge can be tinged with close to 185B; color does not change with development.

*Spadix*.—Length, overall: About 6.3 cm. Length, male flower zone: About 4.5 cm. Length, sterile zone: About 1.5 cm. Length, female flower zone: About 1.8 cm. Diameter, male flower zone: About 9.5 mm. Diameter, sterile flower zone: About 7 mm. Diameter, female flower zone: About 1 cm. Shape: Columnar, spindle-shaped. Apex: Rounded. Base: Obtuse. Aspect: Upright. Color, mature, male zone: Close to 155D. Color, mature, sterile zone: Close to 155D. Color, mature, female zone: Close to 158D. Male flowers: Quantity per spadix: About 160. Shape: Obovate to irregularly shaped. Height: About 3.5 mm. Diameter: About 3 mm. Pollen amount: Sparse to moderate. Pollen color: Close to 9D. Female flowers: Quantity per spadix: About 156. Shape: Obovate. Height: About 2.5 mm. Diameter: About 2 mm. Stigma color: Close to 158D. Ovary color: Close to 159C.

*Scape*.—Length: About 30 cm. Diameter: About 7 mm. Strength: Sturdy; flexible. Aspect: Mostly erect. Texture and luster: Smooth, glabrous; dull to slightly glossy. Color: Close to 147C tinged with close to 146C and with faint stippling, streaks and stripes of close to 200A; just below spathe, glaucous and close to 147C tinged with close to 146C and with faint stippling, streaks and stripes of close to 200A and 200B.

*Seeds and fruits*.—To date, seed and fruit development have not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'OF13-635' as illustrated and described.

* * * * *